United States Patent [19]

Ubukata

[11] Patent Number: 5,813,986
[45] Date of Patent: Sep. 29, 1998

[54] METHOD OF IDENTIFYING THE TIME PHASE OF THE STATE OF AN ORGAN TO BE OBSERVED, AND ULTRASONIC DIAGNOSTIC APPARATUS BASED ON THE SAME

[75] Inventor: Keiichiro Ubukata, Tokyo, Japan

[73] Assignee: GE Yokogawa Medical Systems, Limited, Tokyo, Japan

[21] Appl. No.: 777,751

[22] Filed: Dec. 21, 1996

[51] Int. Cl.⁶ .................................................. A61B 8/00
[52] U.S. Cl. .................................. 600/440; 600/450
[58] Field of Search .................... 128/660.04–660.05, 128/660.07, 661.01, 661.09–661.1, 660.02; 600/440, 441, 443, 447, 450, 456–469

[56] References Cited

U.S. PATENT DOCUMENTS

| | | | |
|---|---|---|---|
| 3,954,098 | 5/1976 | Dick et al. | 128/660.07 X |
| 4,289,141 | 9/1981 | Cormier | 128/713 |
| 4,294,259 | 10/1981 | Picunko et al. | 128/653.1 |
| 5,224,481 | 7/1993 | Ishihara et al. | 128/660.07 |
| 5,241,473 | 8/1993 | Ishihara . | |
| 5,450,850 | 9/1995 | Iinuma | 128/661.09 |
| 5,533,510 | 7/1996 | Koch . | |
| 5,551,434 | 9/1996 | Iinuma | 128/661.09 |

FOREIGN PATENT DOCUMENTS 19524880   7/1996   Germany .

OTHER PUBLICATIONS

IEEE Transaction on Biomedical Engineering; vol. bME–34, 1987, pp. 356–364.

Deutsche Medizinische Wochenschrift (German Mdical Weekly) 109, 1984, pp. 722–727 (English Translation filed herewith) (Schlüter et al).

*Primary Examiner*—Francis Jaworski
*Attorney, Agent, or Firm*—Moonray Kojima

[57] ABSTRACT

A ultrasonic diagnostic apparatus, which is used to inspect the functioning of heart based on ultrasonic images sampled in the expansion period and the contraction period of the heart, includes means of sampling a ultrasonic image of the heart, means of picking up a bionomic signal from the heart, means of memorizing the bionomic signal and ultrasonic image data, means of identifying automatically a time point of inspection to be of the expansion period or the contraction period of the heart based on the bionomic signal read out of the memory means, and means of analyzing the heart functioning based on the ultrasonic images sampled at the time points of inspection and the result of time phase identification.

9 Claims, 4 Drawing Sheets

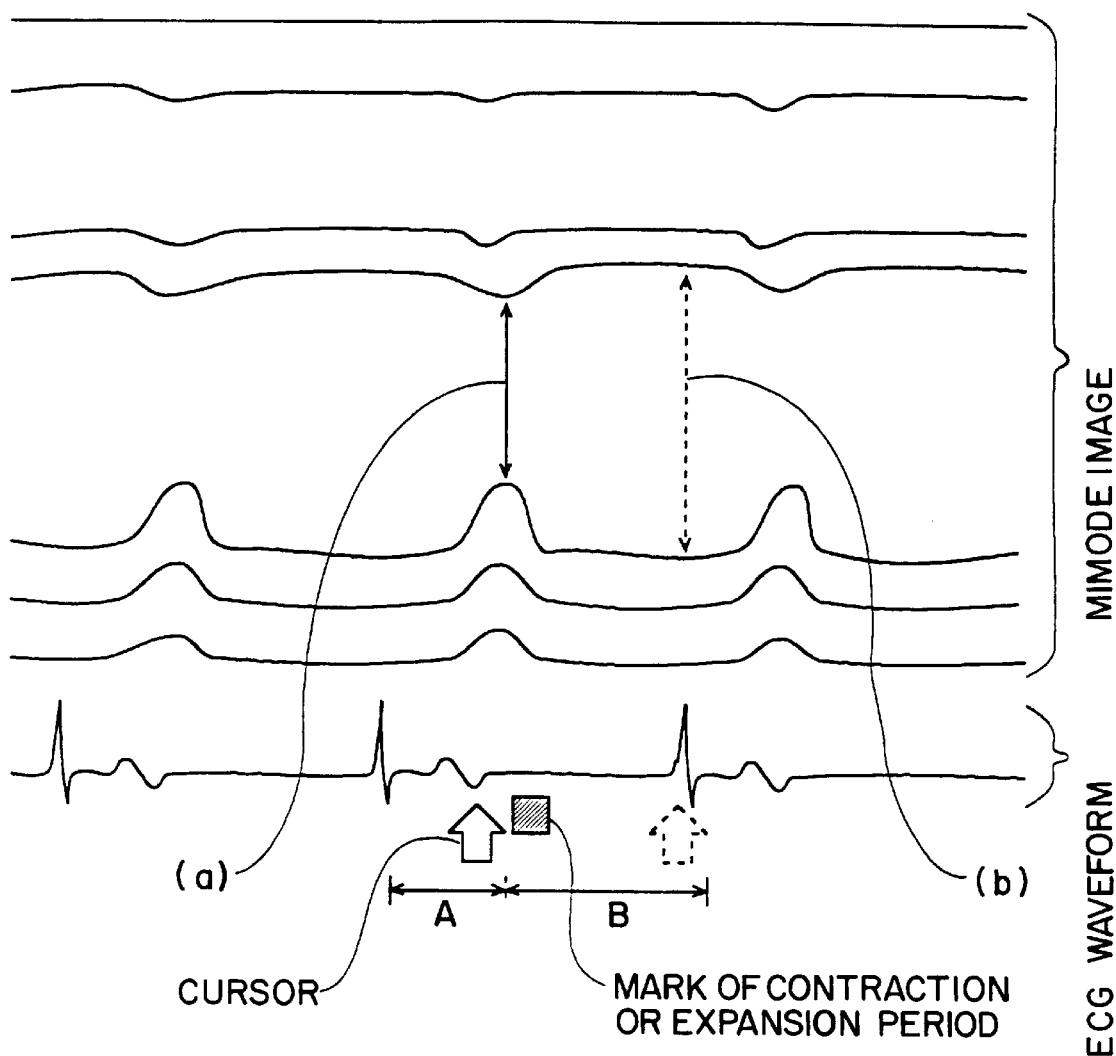

METHOD OF IDENTIFYING THE TIME PHASE OF THE STATE OF AN ORGAN TO BE OBSERVED, AND ULTRASONIC DIAGNOSTIC APPARATUS BASED ON THE SAME

BACKGROUND OF THE INVENTION

1. Field of the Invention

The present invention relates to a method of identifying the time phase of the state of an organ having cyclic expanding and contracting motions used for the inspection of the functioning of the organ based on ultrasonic images, and to a ultrasonic diagnostic apparatus which is used to inspect the functioning of an organ having cyclic expanding and contracting motions based on ultrasonic images by identifying the time phase of organic state automatically.

2. Description of the Related Art

The functioning of an organ having cyclic expanding and contracting motions, e.g., heart, is inspected often based on ultrasonic images. During the inspection of the heart functioning, the volume of heart is calculated from the volume of ventricles and the thickness of cardiac muscles measured in both the expansion and contraction periods of the heart.

Specifically, the end-expansion heart volume is calculated from the ultrasonic data sampled at the end of expansion period and the end-contraction heart volume is calculated from the ultrasonic data sampled at the end of contraction period. The ejection efficiency, the amount of discharge and per-beat discharge, the volume variation graph, etc. are obtained based on the difference between the end-expansion volume and end-contraction volume, and the weight of cardiac muscles is evaluated from their thickness. Dick U.S. Pat. No. 3,954,098, Cormier U.S. Pat. No. 4,289,141; Picunko U.S. Pat. No. 4,294,259; Ishihara U.S. Pat. No. 5,224,481; and Iinuma U.S. Pat. No. 5,450,850 are examples of Prior Art showing the acquiring and determining of various heart functioning parameters, such as Systolic Time Indices (STIs) and volumetric indices using time intervals within contraction and expansion periods of the heart and use of ECG in connection therewith. Various calculations are made using the characteristics of the heart to obtain desired cardiac function parameters.

In dealing with ultrasonic data sampled in the expansion and contraction periods, it is necessary to identify accurately the time phase of the state as to whether the data is of the expansion period or the contraction period.

The conventional inspection based on time line images, such as M-mode image and Doppler images, is carried out as follows. After a sampled image is "frozen" (fixed) and stored in a memory, the end of contraction period is first detected with reference to a bionomic signal, e.g., ECG (electrocardiogram) waveform, which is recorded simultaneously with imaging, and next the cursor is moved to the contraction period on the ECG waveform thereby to sample data of the contraction period. Subsequently, the end of expansion period is detected on the screen, and the cursor is moved to the expansion period on the ECG waveform thereby to sample data in the expansion period.

It is necessary for the inspector to push the data sampling key at a new position (time point) of the cursor and take another key operation for instructing the apparatus that the data sampling time is of the expansion period or the contraction period based on the inspector's own judgement. These steps are usually executed in real time or all executed on stored data. Erroneous entry of the expansion period and the contraction period will produce a wrong analysis result.

On this account, there have been demands of the scheme of automatically identifying the time point of data sampling, i.e., expansion period or contraction period, thereby to reduce the inspector's key operation, and demands of ultrasonic diagnostic apparatus having the automatic time phase identification scheme.

Iinuma U.S. Pat. No. 5,551,434 scans data and stores frames of tomographic data and velocity data, and after completion of scanning, the images are displayed. On the reproduced images, the operator then sets a region of interest (ROI) and obtains from the displayed images, the velocity data corresponding to the ROI. In this manner, the operator does not need to perform both the probing operation and the ROI scanning at the same time. Even with this disclosure, ROI scanning at a contraction period or an expansion period would be based on the experience of the operator.

SUMMARY OF THE INVENTION

Accordingly, an object of the present invention is to provide a method of identifying automatically the time phase of the organic state in terms of the expansion period and the contraction period thereby to reduce the inspector's key operation, and a ultrasonic diagnostic apparatus with the ability of time phase identification.

In a first aspect, the present invention resides in a method of time phase identification for identifying automatically a ultrasonic image sampled at an arbitrary time point to be of the expansion period or the contraction period with reference to a bionomic signal during the inspection based on ultrasonic images sampled in the expansion period and the contraction period of the organ.

The automatically identified time phase is indicated near the cursor on the screen, and it is entered to the ultrasonic diagnostic apparatus so that the inspector's operation is simplified.

In a second aspect, the present invention resides in a ultrasonic diagnostic apparatus used for the organic inspection based on ultrasonic images sampled in the expansion period and the contraction period of the organ, the apparatus including means of memorizing a bionomic signal and ultrasonic image of a live body under test, and means of identifying automatically a ultrasonic image sampled at an arbitrary time point to be of the expansion period or the contraction period with reference to the bionomic signal. The time phase is identified automatically in terms of predetermined time regions centered by the reference position (e.g., R wave) of the bionomic signal read out of the memory means.

In a third aspect, the present invention resides in a ultrasonic diagnostic apparatus used for the inspection of the heart functioning based on ultrasonic images sampled in the expansion period and the contraction period of the heart, the apparatus including means of sampling a ultrasonic image of the heart, means of picking up a bionomic signal, means of memorizing the bionomic signal and ultrasonic image provided by the bionomic signal pickup means and ultrasonic image sampling means, respectively, means of identifying automatically the time point of image sampling to be of the expansion period or the contraction period of the heart, and means of analyzing the heart functioning based on ultrasonic images of the time phases identified by the time phase identifying means.

In the ultrasonic diagnostic apparatus of this aspect, the time phase identifying means is preferably designed to make reference to the R wave which forms a peak of the bionomic signal for the accurate recognition of the time phase of the heart state of an arbitrary time point of inspection.

The time phase identifying means is preferably designed to make reference to predetermined time regions which have been established relative to the R wave in the bionomic signal for the more accurate recognition of the time phase of the heart state of an arbitrary time point of inspection.

In a fourth aspect, the present invention resides in a ultrasonic diagnostic apparatus derived from the second aspect, wherein the apparatus includes means of displaying the bionomic signal and ultrasonic image, and means of entering a time point of inspection on the bionomic signal waveform displayed by the display means so that the time phase identifying means identifies the time phase of the entered time point automatically.

In a fifth aspect, the present invention resides in a ultrasonic diagnostic apparatus derived from the fourth aspect, wherein the memory means stores bionomic signals and ultrasonic images for multiple cycles of organic state and the display means displays a bionomic signal and ultrasonic image read out of the memory means.

In a sixth aspect, the present invention resides in a ultrasonic diagnostic apparatus derived from the fourth aspect or fifth aspect, wherein the bionomic signal is the ECG signal, and the time phase identifying means identifies a time point to be of the expansion period or the contraction period based on the R wave in the ECG signal.

The time phase identification method of the first aspect is capable of identifying the time phase of the state to be of the expansion period or the contraction period automatically.

The ultrasonic diagnostic apparatus of the second aspect is capable of identifying the time phase of the state to be of the expansion period or the contraction period automatically.

The ultrasonic diagnostic apparatus of the third aspect is operative to analyze the heart functioning based on ultrasonic images sampled and stored at multiple time points instructed by the inspector by identifying automatically each time point of inspection to be of the expansion period or the contraction period with reference to the bionomic signal read out of the memory.

Thus, it is possible to provide a ultrasonic diagnostic apparatus capable of identifying the time phase of the state to be of expansion period or the contraction period automatically.

In other words, the invention encompasses an identifying section, wherein time periods of assumed contraction period and expansion period are preselected relative to an ECG R-wave and stored in a memory, and wherein the time periods of assumed contraction and expansion are taken from the identifying section and displayed so that an operator can readily determine the time period (e.g. contraction period or exapnsion period of the heart) at which the operator enters instructions for taking measurements of the heart.

In this manner, as distinguished from the prior art, the operator no longer has to rely on his own experience and judgement as to occurrence of the contraction period or expansion period to key in instructions at the desired contraction or expansion period. Thus, the invention increase reliability, reduces risk of the operator operating the instruction key at wrong time period, and reduces time of diagnosis, and thereby also increase efficiency.

Other objects and advantages of the present invention will be apparent from the following description of the preferred embodiment of the invention as illustrated in accompanying drawings.

BRIEF DESCRIPTION OF THE DRAWINGS

FIG. 3 is a waveform diagram used to explain M-mode image and a bionomic signal displayed on the screen.

DESCRIPTION OF THE PREFERRED EMBODIMENTS

Figure 1:
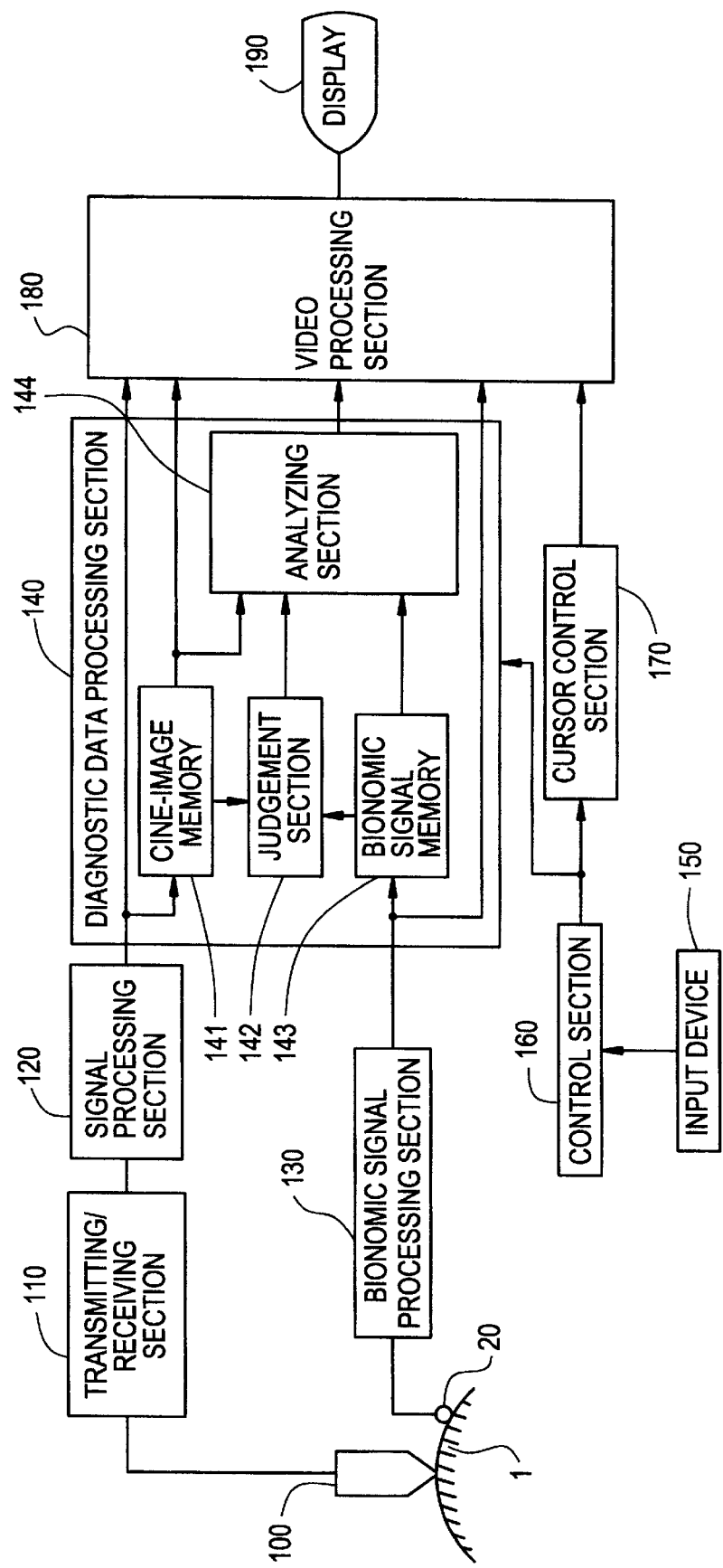
FIG. 1 is a block diagram showing the arrangement of the ultrasonic diagnostic apparatus based on an embodiment of this invention.

The inventive ultrasonic diagnostic apparatus will be explained with reference to FIG. 1, first for its structure and basic operations of individual functional sections.

A live body 1 to be inspected includes an organ having cyclic expanding and contracting motions, which is assumed to be the heart in this embodiment. A probe 10 is used to emit and receive ultrasonic waves to/from the body 1, and an electrode 20 is used to pick up a bionomic signal from the body 1.

A transmitting/receiving section 110 produces and sends a ultrasonic wave to the probe 10 and implements various reception processes for a return ultrasonic wave detected by the probe 10. A return signal resulting from the processes by the transmitting/receiving section 110 is rendered various signal processings by a signal processing section 120 so that data used in various inspection modes are produced.

A bionomic signal processing section 130, which receives the bionomic signal detected by the electrode 20, processes the signal to produce an ECG waveform which represents the electrogram (potential of muscles).

A diagnostic data processing section 140 receives the return signal processed by the signal processing section 120 and the bionomic signal processed by the bionomic signal processing section 130, and analyzes the heart functioning by identifying the time phase of expansion period or contraction period for the return signal. The diagnostic data processing section 140 includes a cine-image memory 141 for storing image data provided by the signal processing section 120, another memory 143 for storing bionomic signals, an identifying section 142 which identifies the time phase of the heart state at an arbitrary instructed time point with reference to preset time regions established relative to the R wave of the bionomic signal, and an analyzing section 144 which implements the analysis of the heart functioning of the instructed time point.

An assortment of input devices 150 used by the inspector for entering instructions and data include a keyboard, a tablet, a mouse device and a trackball. In this embodiment, the keyboard is used for specifying time points for the analysis of heart functioning.

A control section 160 controls the overall apparatus, and particularly it controls the display screen in response to the input from the keyboard 150 and controls the process of the analyzing section 144.

A cursor display section 170 operates under control of the control section 160 to generate signals for displaying a cursor which indicates a time point entered by the inspector with the keyboard 150.

A video processing section 180 produces a ultrasonic image signal from the image data provided by the signal processing section 120, a cursor signal from the signal provided by the display section 170 and a display signal of the frame of the analysis result provided by the analyzing section 144, and merges these signals into a video signal.

A display device 190 produces a picture on the screen from the video signal provided by the video processing section 180.

Figure 2:
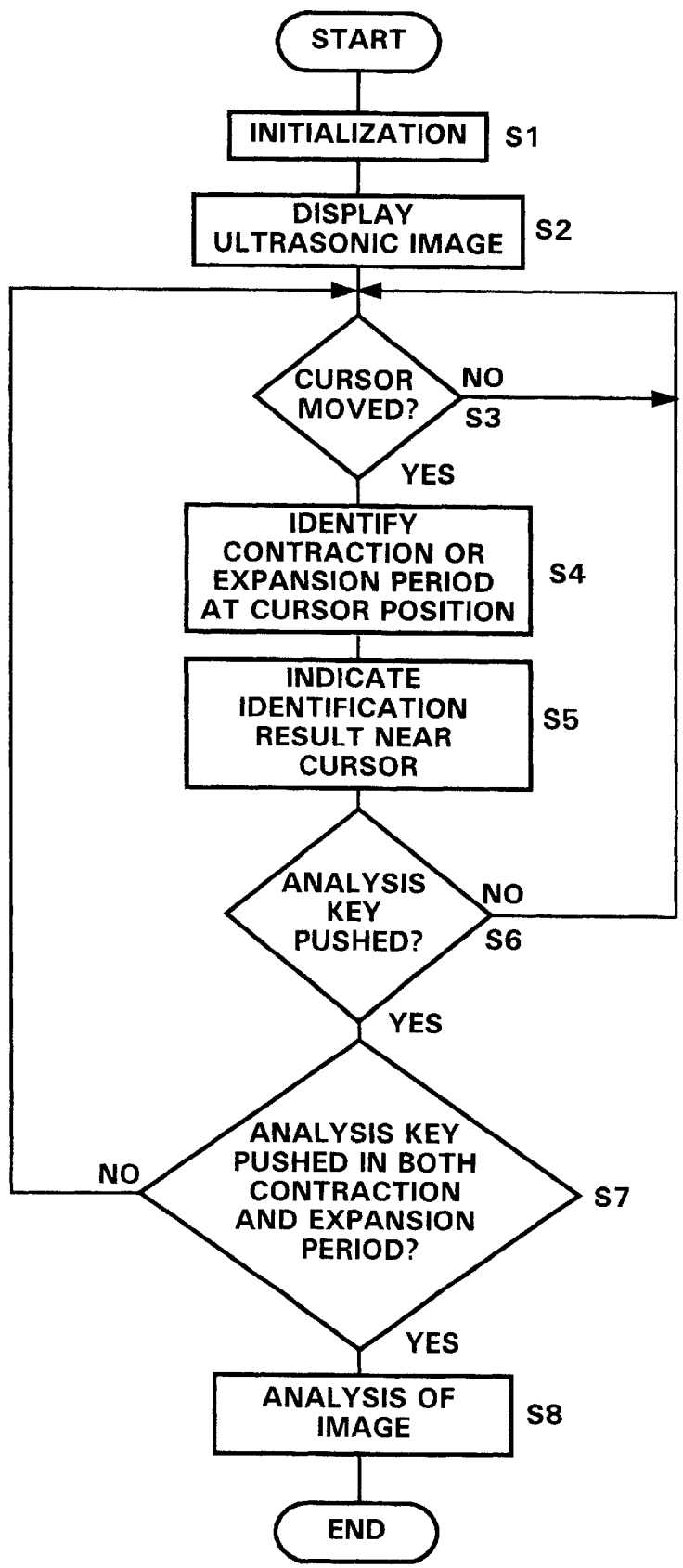
FIG. 2 is a flowchart showing the processes of the time phase identification method based on an embodiment of this invention.

Next, the operation of time phase identification of the ultrasonic diagnostic apparatus arranged as described above will be explained with reference to the flowchart of FIG. 2.

At starting, the control section 160 initializes all functional sections: (step S1). The transmitting/receiving section 110 generates a ultrasonic signal, and the probe 10 emits a beam of ultrasonic wave to the body 1 and receives a reflected ultrasonic wave from the body 1.

The transmitting/receiving section 110 implements the reception process for the return ultrasonic wave, and the signal processing section 120 processes the return signal to produce image data of any of B mode, M mode and Doppler mode.

During these processes, the electrode 20 picks up a bionomic signal from the body 1, and the bionomic signal processing section 130 processes the signal to produce bionomic signal data.

The video processing section 180 produces a video signal from the image data and bionomic signal data, and the display device 190 displays the image of the video signal on the screen: (step S2) . For example, the display device 190 displays a B-mode image and a bionomic signal, or a set of M-mode image and a bionomic signal depending on the process carried out by the signal processing section 120.

FIG. 3 shows, in a sense of model, a display on the screen, which includes a set of M-mode image resulting from a ultrasonic beam emission to the observation position of the ventricles of heart and an ECG waveform of the bionomic signal displayed on the common time axis. The time passes on from left to right on the screen.

For the analysis of the heart functioning, which will be explained later, the inspector can move the cursor along the time axis by operating the keys on the keyboard 150.

Figure 4A:
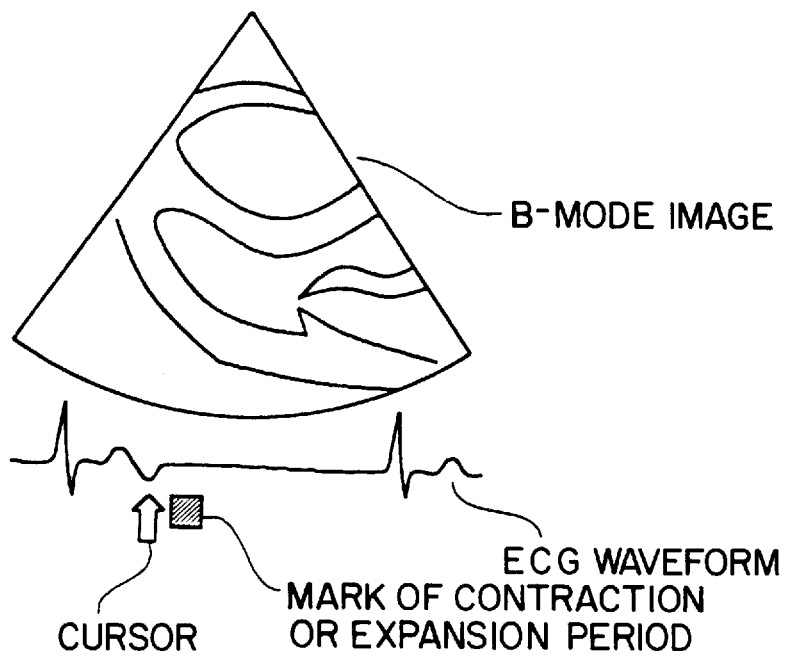
FIGS. 4A and 4B are waveform diagrams used to explain B-mode images and bionomic signals displayed on the screen.
Figure 4B:
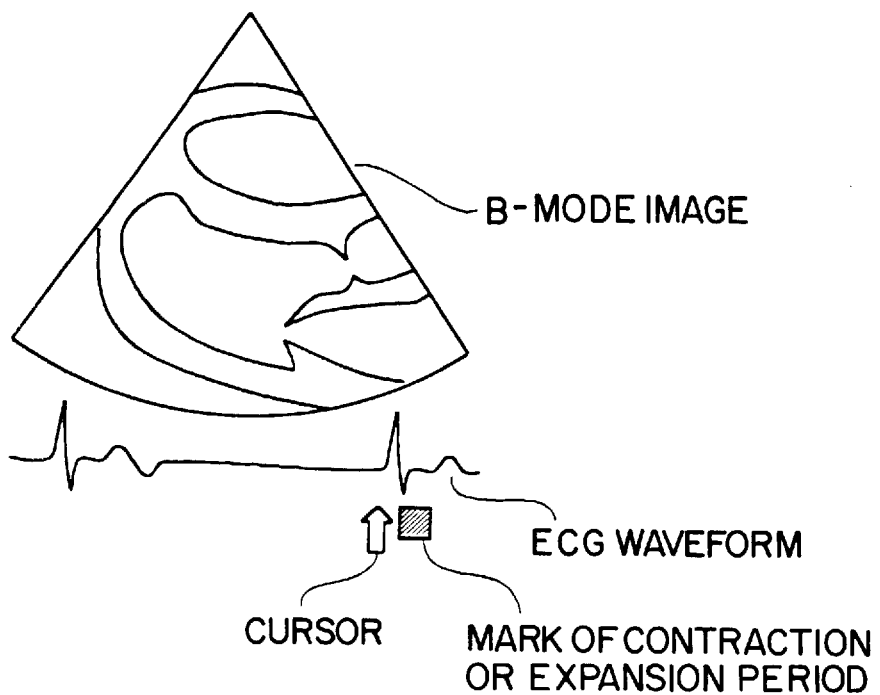

FIGS. 4A and 4B show displays on the screen each including a B-mode image sampled at a certain time point and an ECG waveform of the bionomic signal. For the analysis of the heart functioning, which will be explained later, the inspector can move the cursor along the time axis by operating the keys on the keyboard 150, and a B-mode image of the time pointed by the cursor is displayed. FIGS. 4A and 4B show B-mode images sampled at different time points specified by the cursor positions.

By setting the time span of the screen so that at least two R waves of the ECG waveform appear, i.e., displays of FIG. 3 and FIG. 4 include three and two R waves, respectively, it is possible to observe at least one complete cycle of heart state including an expansion period and a contraction period for the analysis.

With the ultrasonic image and bionomic signal waveform being displayed, the inspector can instruct the "freezing" of display by operating the keyboard 150 at an intended time point, and the sampling of image and waveform is suspended and data at that time point are memorized in the cine-image memory 141 and bionomic signal memory 143 for the later review or analysis. The inspector can now move the cursor to another observation time point.

The cine-image memory 141 has a capacity for sequentially storing multiple e.g., generally one hundred or more, frames of image data produced by the signal processing section 120. In response to the inspector's image freezing instruction with the keyboard 150, the control section 160 suspends the storing of image data in the cine-image memory 141, and the inspector proceeds to the following operational stage.

The inspector operates the forward/backward keys on the keyboard 150 to move the cursor to the position of ECG waveform that seems to indicate the end of contraction period or expansion period. The control section 160 responds to the instruction signal from the keyboard 150 to operate on the cursor control section 170 to reposition the cursor on the screen as instructed. The diagnostic data processing section 140 also responds to the cursor moving instruction signal from the keyboard 150 to identify the time phase of the heart state at the new cursor position, i.e., whether the time point is in the contraction period or expansion period.

Specifically, the identification section 142 identifies the time pointed by the cursor in terms of the preset time regions relative to the R wave of the bionomic signal: (step S4 in FIG. 2), and indicates the result of identification near the cursor on the screen as shown by a small hatched square in the examples of FIG. 3 and FIGS. 4A and 4B: (step S5).

Making reference to the R wave, which is the peak of the bionomic signal, facilitates the determination of time point and enables accurate identification of the time phase. It also ensures the coverage of one complete cycle of state including a contraction period and expansion period for the identification of time phase and the analysis of heart functioning.

As to the result of identification of the time phase at the cursor position, indication whether the time point is in the contraction period or the expansion period is displayed near the cursor. A display position is shown by a small hatched square in the examples of FIG. 3 and FIGS. 4A and 4B.

When the inspector instructs on the keyboard 150 the analysis at the time point of inspection (contraction period or expansion period) pointed by the cursor: (step S6), a series of image data from the freeze time T back to the cursor position t, i.e., image data of period T-t, are read out of the cine-image memory 141 to the analyzing section 144.

Specifically, ultrasonic image data of the contraction period (e.g., image data indicated by (a) at the time point of the solid cursor symbol) and a flag indicative of the contraction period imparted by the identification section 142 are first loaded into the analyzing section 144. Subsequently, in response to the inspector's instructions of cursor movement and commencement of analysis, image data of the expansion period (e.g., image data indicated by (b) at the time point of the dashed cursor symbol in FIG. 3) and a flag indicative of the expansion period imparted by the identification section 143 are loaded into the analyzing section 144: (steps S3–S7 in FIG. 2).

The identification section 142 has the presetting of a time range from 50 ms to 300 ms following the R wave of ECG waveform (indicated by A for explanation in FIG. 3) as a time region for the presumed contraction period, and another time range from 300 ms following the R wave to 50 ms following the next R wave (indicated by B for explanation in FIG. 3) as a time region for the presumed expansion period, thereby making a judgement of the contraction period or expansion period for the time point of inspection instructed by the inspector.

That is to say, the indentification section 142 has previously stored therein preset time ranges (e.g. as shown in FIG. 3, time periods "A" and "B") corresponding to a contraction period and an expansion period. Going to FIG. 3, the presumed time periods are measured from ECG R-wave (i.e. the largest voltage spikes of the ECG) as being the zero time and the presumed contraction period being measured from a time point which is 50 ms from the R-wave zero point to a time point which is 300 ms from the R-wave zero point. Thus, the time period of the presumed contraction period is 300 ms–50 ms=250 ms. The time axis is measured from the R-wave as being zero. The presumed contraction period is shown as "A" in FIG. 3. On the other hand, the presumed expansion period is measured from the end of the contraction period, that is in this case at 300 ms from the first R-wave, to 50 ms from the next succeeding R-wave. This is shown as period "A" in FIG. 3. The time period "B" would thus depend on when the next R-wave occurs, and is measurable since the ECG R-waves are readily determinable.

The time periods "A" and "B" are identified and stored as signals in the identification section 142 so as to be accessed when desired by the control section 160 and provide time phase identification to analysis section 144 and for display in display 180.

The ultrasound scanning results may be stored in memory 120, and the ECG signals may be stored in memory 143 for later analysis by analyzer 144. When the operator desires to scan the organ, such as human heart, by placing the cursor at the desire time range "A" or "B", the scanning of the heart can take place automatically in such contraction or expansion phase of the heart, and, advantageously, without requiring human judgement or experience to determine where exactly is the contraction or expansion phase, as was necessary in the prior art.

Advantageously, the "presumed" contraction and expansion periods are "preset" in the identification section 142. As shown more clearly in FIG. 3, the preset time periods are obtained by observing the R-wave of the ECG, and then measuring, e.g. 50 ms to 300 ms, from that R-wave as the zero point, to define the presumed contraction period, and then, at the end of the presumed contraction period (e.g. 300 ms) laying out the expansion period as being from such end of the contraction period to a time, for example 50 ms, after the next succeeding R-wave of the ECG. The preset presumed contraction period and expansion period are made accessible to the operator, such as by display of the R-wave and ultrasound images. Thus, advantageously, by mere observation, the operator automatically knows where to place the cursor to start the scanning of the heart during the contraction or expansion period selected by the operator. Advantageously, this results in a more reliable scan, more efficiency, and reduced time of scanning and diagnosis. These functions can also be done automatically with use of suitable computers and associated devices.

The presumed contraction and expansion periods can be suitable adjusted as desired to suit the purpose of diagnosis. For example, the presumed contraction period of the example is 250 ms, but can be extended or reduced. The following expansion period, can then be either extended or reduced. The contraction and expansion periods can be readily ascertained for different organs, such as the heart by studying the ECG signals.

The other circuit and system components are those known in the art, and the obtaining of the various functional parameters, for example, of the heart, are also known in the art. The invention improves upon such art by uniquely defining presumed contraction period and expansion period utilizing the R-wave of the ECG signal, and recording such time periods for display to an operator who can then utilize such presumed contraction period and expansion period to pin point exactly when to scan the heart, either in the contraction period or the expansion period, and this is done without error as was possible in the prior art when determination of the contraction or expansion period was based on experience of the operator and thus subject to human errors.

Upon receiving the image data of the contraction period and expansion period and the identification result on the time phase of the heart state, the analyzing section 144 carries out the analysis of heart functioning by calculating the differences and ratios of the data: (step S8 in FIG. 2). The result of analysis is displayed on the display device 190, and at the same time it is transferred to an external processor or data storage unit via data bus (not shown).

According to the present invention, as described above, the inspector is merely required to operate the keyboard 150 to move the cursor for tracing back the cine-image and instruct the commencement of analysis.

As a result, the instruction of the contraction period or expansion period based on the inspector's judgement that has been required in the conventional apparatus is eliminated by the automated time phase identification process, whereby the operationability of the inspection apparatus is improved and wrong analysis results caused by human error of the judgement of period can be eliminated.

What is claimed is:

1. In an ultrasound method of diagnosing characteristics of an organ having a contraction period and an expansion period, comprising the steps of
    ultrasonically scanning sections of the organ with application and reflection of ultrasound signals;
    obtaining bionomic signals of a body containing the organ;
    storing the bionomic signals; and
    providing ultrasonic images of the sections of the organ at a selected inspection time with the signals provided by the ultrasound scanning and utilizing the bionomic signals; the improvement comprising:
        preselectively storing time periods of assumed contraction period and expansion period of the organ as measured from a spike of the bionomic signals; and
        selectively inspecting said organ by directing the ultrasound scanning of the sections of the organ at a time within the time period of the assumed contraction or expansion period without having to estimate the time period of the contraction or expansion period.

2. The method of claim 1, wherein said bionomic signals are ECG signals, and said spikes are R-waves thereof, and wherein said organ is a heart.

3. The method of claim 2, wherein said ultrasound images are stored for a plurality of cycles.

4. The method of claim 2, wherein said ultrasound images are said ECG waves are displayed on a display means; and wherein the selected inspection time occurs during the assumed contraction period or expansion period as displayed on the ECG wave.

5. In an ultrasound diagnostic apparatus used for inspection of an organ functioning based on ultrasound images sampled in a contraction period or expansion period of the organ, and comprising:
    means for providing ultrasound sampling of sections of the organ;
    means for concurrently obtaining a bionomic signal of a body containing the organ;

memory means for storing images produced from the ultrasound samplings and for storing bionomic signals from the means for obtaining the bionomic signals; and means for analyzing the functioning of the organ from the images and bionomic signals stored in the memory means and for providing parameters of the organ thereby; the improvement comprising:

means for preselectively storing in said analyzing means marks which identify assumed contraction period and expansion period of the organ by selectively obtaining time location of spikes in the bionomic signals for the end of the expansion period and the end of the contraction period of the organ; and means for providing the marks preselectively stored in the analyzing means so that an operator can readily determine the location of a cursor on a time scale providing identification of the contraction period and expansion period of the organ.

6. The apparatus of claim 5, wherein said memory means comprises means for storing a plurality of cycles of the ultrasound samplings and said bionomic signals.

7. The apparatus of claim 6, wherein said means for providing comprises display means for display means for displaying said plurality of cycles of ultrasound images from said samplings and of said bionomic signals.

8. The apparatus of claim 5, wherein said organ is a heart, and wherein said bionomic signals are ECG signals, and said spike is an R-wave thereof.

9. The apparatus of claim 8, further comprising display means for displaying said ultrasound images and said ECG signals; and means for entering an inspection time point on said ECG signal waves displayed in said display means; and means for indicating automatically which of the assumed contraction time range and expansion time range the inspection point is placed.

* * * * *